US00PP25064P3

(12) United States Plant Patent
Austin

(10) Patent No.: US PP25,064 P3
(45) Date of Patent: Nov. 18, 2014

(54) ***ROSA HYBRIDA* SHRUB NAMED 'AUSCOUSIN'**

(50) Latin Name: *Rosa hybrida*
Varietal Denomination: AUScousin

(71) Applicant: David Austin Roses Ltd., Wolverhampton (GB)

(72) Inventor: David J. C. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 40 days.

(21) Appl. No.: 13/986,067

(22) Filed: Mar. 28, 2013

(65) Prior Publication Data
US 2014/0075606 P1 Mar. 13, 2014

(51) Int. Cl.
*A01H 5/00* (2006.01)

(52) U.S. Cl.
USPC ..... Plt./106

(58) Field of Classification Search
USPC ..... Plt./106, 105, 107
See application file for complete search history.

*Primary Examiner* — Kent L Bell
(74) *Attorney, Agent, or Firm* — KPPB LLP

(57) ABSTRACT

A variety of rose plant of the shrub class, named 'AUScousin', suitable for repeat flowering production having blooms of rich salmon color that commence as a red bud and open to pretty cups that then develop into perfectly formed rosettes having a medium-strong myrrh fragrance.

1 Drawing Sheet

Classification: The present invention relates to a new *Rosa hybrida* shrub.

Variety denomination: The new plant has the varietal denomination 'AUScousin'.

CROSS-REFERENCE TO RELATED APPLICATIONS

The current application claims priority to a European Plant Breeder's Rights Application No. 2012/1945, filed Sep. 12, 2012, the disclosure of which is incorporated herein by reference.

ORIGIN OF INVENTION

This invention relates to a new and distinct variety of shrub rose plant named 'AUScousin', which was originated by crossing two unnamed, unpatented varieties of *Rosa hybrida*.

BACKGROUND OF THE INVENTION

The primary objective of this breeding was to grow a vigorous and healthy rose growing as a medium sized upright shrub and having blooms of rich salmon color that commence as a red bud and open to pretty cups that then develop into perfectly formed rosettes having a medium-strong myrrh fragrance.

SUMMARY OF THE INVENTION

Among the features which distinguish the new variety from other presently available and commercial rose cultivars known to the inventor is the following combination of characteristics: salmon colored, rosette shaped blooms, a medium-strong myrrh fragrance, and dark green, glossy foliage with vigorous growth.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUScousin' may be asexually propagated by budding. The budding successfully occurred on the plant/rootstock *Rosa* cv. 'Dr. Huey' in the United States, and on the plant/rootstock *Rosa dumetorum* cv. 'Laxa' in the United Kingdom.

COMPARISON WITH PARENTS

The new rose may be distinguished from its seed parent, by the following combination of characteristics: whereas the seed parent is apricot in color, 'AUScousin' bears flowers of salmon-pink: The new variety is classified as a *hybrida* rose.

The new variety may be distinguished from its pollen parent, by the following combination of characteristics: whereas the pollen parent bears looser petalled apricot blooms, 'AUScousin' bears flowers of salmon-pink.

COMPARISON WITH THE CLOSEST COMMERCIALLY AVAILABLE CULTIVAR

The closest commercially available cultivars to the new variety are the 'AUShunter' (U.S. Plant patent application Ser. No. 10/615,742, Abandoned) and 'AUSencart' (Australia PBR App. No. 2002/076). The new rose may be distinguished from the 'AUShunter' variety by the following combination of characteristics: 'AUShunter' forms a larger shrub than 'AUScousin' reaching 1.25 m, and has fruity fragrance with hints of lemon and raspberry, whereas 'AUScousin' is a smaller shrub reaching only 1 meter and has a myrrh fragrance. Likewise, the new rose may be distinguished from the 'AUSencart' variety by the following combination of characteristics: 'AUSencart' is redder in color with a fruity fragrance, whereas 'AUScousin' is more salmon colored with a myrrh fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

The following description is of 1 year-old rose plants of the new variety grown outdoors in Albrighton, Britain in the month of July. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

- *Size*.—About 2 cm long and 1.8 cm in diameter when the petals start to unfurl.
- *Form*.—The bud form is globular.
- *Color*.—When sepals first divide, the bud color is red (RHS 51A). When half blown, the upper sides of the petals are RHS 39A, and the lower sides of the petals are RHS 41C.
- *Calyx*.—Shape: star-shaped when flower fully opened, with sepals folding back. Length: 7 cm. Diameter: 7 cm.
- *Sepals*.—Arrangement: Regular. Color: Upper Surface: Yellow-Green (RHS 146D). Lower Surface: Yellow-Green (RHS 144B). Length: 32 mm. Width: 10 mm. Shape: Lanceolate. Surface texture: Upper Surface: Downy. Lower Surface: Glandular. Number: There are three normally appendaged sepals. There are 2 unappendaged sepals with slightly hairy edges.
- *Receptacles*.—Color: Green (RHS 143B). Shape: Funnel. Size: medium, about 1 cm×0.9 cm. Surface: Smooth.
- *Peduncle*.—Length: medium, averaging about 8.5 cm. Surface: prickly. Color: Light green (146C) with some red (RHS 39A). Strength: Normal.

Blooms:

- *Size*.—Large, average open diameter is about 9 cm.
- *Borne*.—Mostly singly in clusters of 1-4 blooms having flat shape.
- *Stems*.—Strength: Strong, average length is about 6 cm. Diameter: 5 mm.
- *Form*.—When first open, bloom is cupped. Permanence of bloom: outer petal edges curl slightly.
- *Petalage*.—Number of petals under normal conditions: 78.
- *Color*.—The upper sides of the petals are Red-Purple (RHS 62B). The reverse sides of the petals are Red-Purple (RHS62B) with Yellow (RHS 1D). The base of the petals is Yellow (RHS 1D).
- *Variegations*.—Outer side, Pink Yellow blend.
- *Discoloration*.—The general tonality at the end of the first day is (RHS 39B) and at the end of the third day is (RHS 62C) with RHS (1D).
- *Fragrance*.—Moderate strong. Character of fragrance: Myrrh.

Petals:

- *Texture*.—Smooth.
- *Size*.—Width: 3 cm. Length: 3.5 cm.
- *Surface*.—Smooth.
- *Shape*.—Obovate.
- *Margin*.—Some notched, some entire.
- *Apex shape*.—Rounded.
- *Base shape*.—Outer petals: obtuse; Inner petals: pointed.
- *Form*.—Outer petals slightly incurved.
- *Arrangement*.—Imbricated.
- *Petaloids*.—Number: 17. Color: Petal: RHS 43D; Anther: RHS 13A; Filament: RHS 12A. Length: Petal: 10-13 mm. Anther: 2-5 mm. Filament: 4-6 mm. Width: Petal: 1-1.5 mm. Anther: 2 mm. Filament: 0.1-1 mm. Shape: Irregular. Margin: Irregular.
- *Persistence*.—Petals hang on and dry.
- *Lastingness*.—On the plant: fair, about 5 days. As a cut flower: not tested.

Reproductive parts:

- *Stamens*.—Number: 140. Length: 10 mm.
- *Anthers*.—Length: 2-3 mm. Color: Yellow (RHS 13A). Arrangement: Mixed with petaloids.
- *Filaments*.—Color: Yellow (RHS 12A) with some red (RHS 47C). Length: 5-10 mm.
- *Pollen*.—Color: Yellow (RHS 13A).
- *Pistils*.—Number: 60. Length: 6.5 mm.
- *Styles*.—Color: Pink and Yellow-Green (RHS 43D & RHS 1D). Length: 6 mm.
- *Stigmas*.—Color: Yellow (RHS 16A). Length: 0.5 mm.
- *Hips*.—None Observed.

PLANT CHARACTERISTICS

Plant form: Shrub.

Plant growth: Vigorous, upright, bushy.

Age to maturity: Two years.

Mature plant: Height: 90 cm. Width: 60 cm.

Rootstock: *Rosa* 'Dr. Huey' for U.S. and *Rosa dumetorum* cv. 'Laxa' for observed plants in the U.K.

Foliage:

- *Number*.—Leaflets on normal mid-stem leaves is: 5 (including terminal leaflet).
- *Size*.—Medium, about 13 cm long×10 cm wide.
- *Quantity*.—Abundant. Number of leaves per flowering stem is: 9.
- *Color*.—New foliage: Upper side: Yellow-Green Group (RHS 146B). Lower side: Yellow-Green RHS (146C), both upper and lower tinged RHS 183C. Old foliage: Upper side: Green (RHS 139A). Lower side: Green Group (RHS 138A).

Leaflets:

- *Size*.—About 5.8 cm long×3 cm wide.
- *Shape*.—Oval.
- *Base shape*.—Obtuse.
- *Apex shape*.—Acuminate.
- *Texture*.—Smooth.
- *Edge*.—Serrated.
- *Serrations*.—Single.

*Petiole*.—Color: Yellow/Green (RHS 146B). Length: 3 cm. Width: 1.5 mm. Surface Texture: with prickles.

*Petiole rachis*.—Color: Yellow/Green Group (RHS 146B). Underside: with prickles.

*Stipules*.—Length: 2 cm, glandular. Color: Green (146B).

*Auricle*.—Shape: Lanceolate. Length: 0.8 cm. Width: 2 mm. Color: Yellow-Green (RHS 146B).

*Vein color*.—As leaf color.

*Venation pattern*.—Reticulate (net-veined).

Wood:

*New wood*.—Color: Yellow-Green (RHS 143B) with some Red-Purple (RHS 58A). Bark: Smooth.

*Old wood*.—Color: Yellow-Green (RHS 146B). Bark: Smooth.

Branching habit:

*Number*.—4-6 per main stem.

*Lateral branch dimensions*.—Length: 40 cm. Diameter: 10 mm.

Stems:

*Mature stem*.—Length: 15 cm. Diameter: 7 mm.

*Internode distance*.—4-10 cm. The above measurements are all variable, depending on growing conditions in a season.

*Stem pubescence present*.—No.

Prickles:

*Quantity*.—On main canes from base: few. Number per stem length: 6 per 30 cm. On laterals from main canes: many. Number per stem length: 10 per 10 cm.

*Form*.—Deep concave.

*Length*.—7-8 mm.

*Color when young*.—Red (RHS 181A).

*Color when mature*.—Red (RHS 181A).

Small prickles:

*Quantity*.—Main stalk: None.

Disease resistance:

*Mildew*.—Resistant.

*Blackspot*.—Resistant.

*Rust*.—Resistant.

Pest resistance: Not tested.

Winter hardiness: Not tested.

Growing conditions: Normal.

What is claimed is:

1. A new and distinct variety of rose plant of the shrub class suitable for repeat flower production, substantially as herein shown and described.

* * * * *

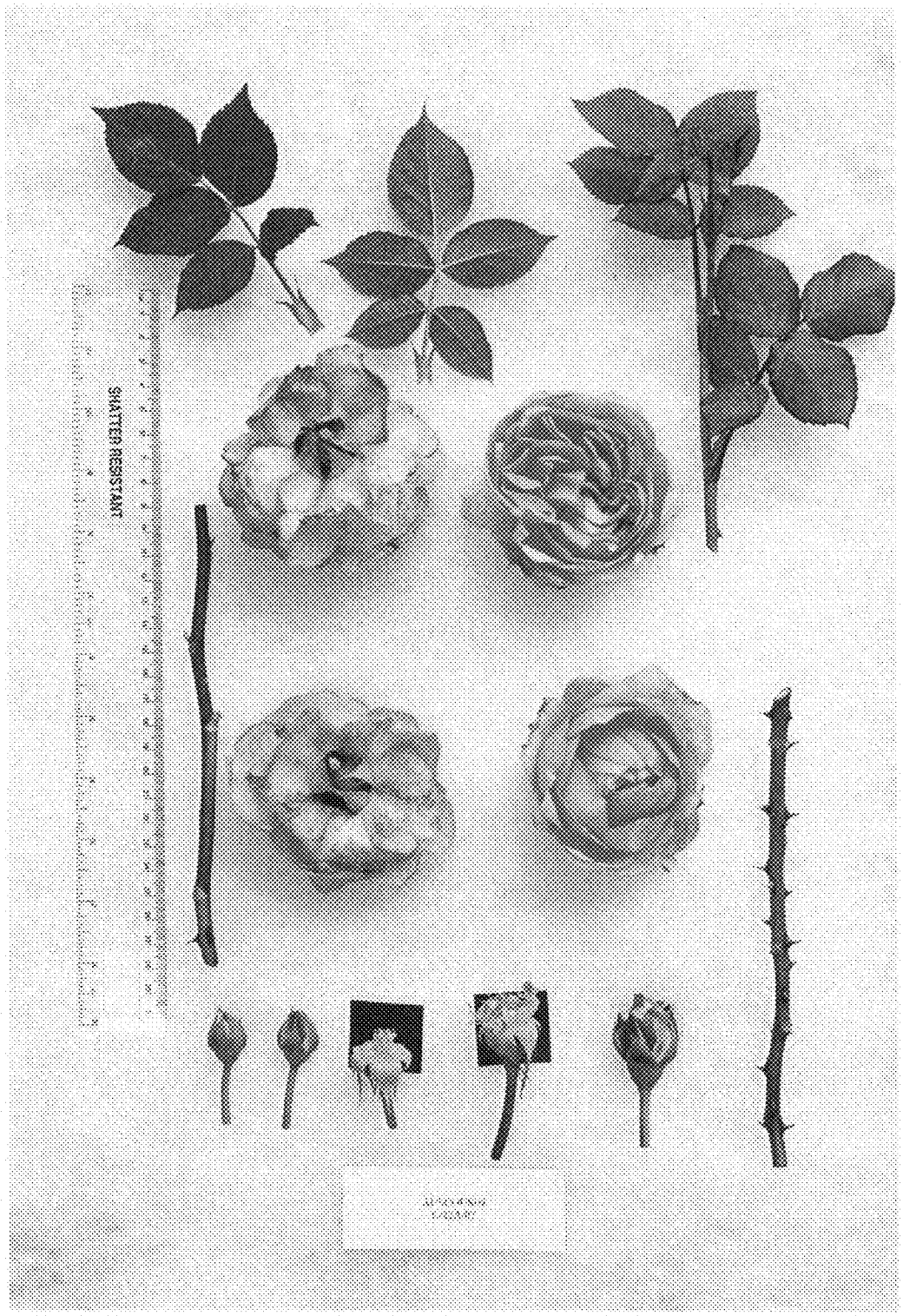
SHATTER RESISTANT